United States Patent
Meckler et al.

(10) Patent No.: US 7,498,345 B2
(45) Date of Patent: Mar. 3, 2009

(54) PROCESS FOR PRODUCTION OF PIPERIDINE DERIVATIVES

(75) Inventors: Harold Meckler, Delmar, NY (US); Benjamin J. Littler, Somerville, MA (US); Prasad Raje, Glenmont, NY (US); Michael Van Brunt, Covington, WA (US); Paul F. Vogt, Albany, NY (US)

(73) Assignee: Albany Molecular Research, Inc., Albany, NY (US)

( * ) Notice: Subject to any disclaimer, the term of this patent is extended or adjusted under 35 U.S.C. 154(b) by 395 days.

(21) Appl. No.: 10/943,276

(22) Filed: Sep. 17, 2004

(65) Prior Publication Data

US 2006/0063808 A1    Mar. 23, 2006

(51) Int. Cl.
*A61K 31/445* (2006.01)
(52) U.S. Cl. ...................... 514/317; 546/235
(58) Field of Classification Search ................ 514/317; 546/235
See application file for complete search history.

(56) References Cited

U.S. PATENT DOCUMENTS

| | | | |
|---|---|---|---|
| 3,806,526 A * | 4/1974 | Carr et al. ............... | 546/190 |
| 4,254,129 A | 3/1981 | Carr et al. | |
| 4,254,130 A | 3/1981 | Carr et al. | |
| 4,550,116 A | 10/1985 | Soto et al. | |
| 5,589,487 A | 12/1996 | D'Ambra | |
| 5,994,549 A | 11/1999 | D'Ambra | |
| 6,057,456 A | 5/2000 | Hartwig et al. | |
| 6,242,606 B1 | 6/2001 | Krauss et al. | |
| 6,743,941 B2 | 6/2004 | Schroeder et al. | |
| 6,777,555 B2 | 8/2004 | Krauss et al. | |

FOREIGN PATENT DOCUMENTS

| | | | |
|---|---|---|---|
| DE | 2303245 | * | 8/1973 |
| WO | WO 94/03170 | | 2/1994 |
| WO | 95/00480 | | 1/1995 |
| WO | 95/00482 | | 1/1995 |
| WO | 97/22344 | | 6/1997 |
| WO | WO 2005/077884 | | 8/2005 |

OTHER PUBLICATIONS

Sakamoto et. al. "Synthesis of methyl 2-(Heteoraryl)propanolates via palladium catalyzed reaction" Heterocycles 1993, 36, 2509-2512.*
Dorwald F. A. Side Reactions in Organic Synthesis, 2005, Wiley: VCH, Weinheim p. IX of Preface and Chapter 8, pp. 279-308.*
Agnelli et. al. "Synthesis of Arylacetates by the Palladium-catalyzed Cross-Coupling of Aryl Bromides and Copper (II) Enolates" Tetrahedron Letters 1998, 39, 8807-8810.*
Hama, et. al. "Palladium-Catalyzed Arylation of Esters and Amides under More neutral Conditions" Journal of The American Chemical Society 2003, 125, 11176-11177.*
Carfagna, Carla; Musco, Alfred; Sallese, Gianna; Sanit, Roberto; Fiorani, Tiziana "Palladium-Catalyzed Coupling Reactions of Aryl Triflates or Halides with Ketene Trimethylsilyl Acetals. A New Route to Alkyl 2-Arylakanoates" Journal of Organic Chemistry, 1991, 56, 261-263.*

Millard, A.A.; Rathke, Michael W. "A Nickel Catalyst for the Arylation and Vinylation of Lithium Ester Enolates" Journal of the American Chemical Society 1977, 99, 4833-4835.*
Ei-ichi Negishi Handbook of Organopalladium Chemistry for Organic Synthesis, John Wiley & Sons, 2002, 215-227.*
Darcy Ann Culkin "Synthesis and Reactivity of Palladium Complexes of Functionalized Alkyls. Selection of Catalysts for the alpha-Arylation of Nitriles and Amides" Yale University May 2004 p. 2, 12-40.*
Stephen H. Kawai, Robert J. Hambaleck and George Just, "A Facile Synthesis of an Oxidation Product of Terfenadine", *J. Org. Chem*, 59, 2620-2622 (1994).
Morten Jorgensen, Sunwoo Lee, Xiaoxiang Liu, Joanna P. Wolkowski, and John F. Hartwig, "Efficient Synthesis of a-Aryl Esters by Room-Temperature Palladium-Catalyzed Coupling of Aryl Halides with Ester Enolates", *J. Am. Chem. Soc.* 124, 12557-12565 (2002).
Xiaoxiang Liu and John F. Hartwig, "Palladium-Catalyzed Arylation of Trimethylsilyl Enolates of Esters and Imides. High Functional Group Tolerance and Stereoselective Synthesis of a-Aryl Carboxylic Acid Derivatives", *J. Am. Chem. Soc.* (2004) 126, 5182-5191.

* cited by examiner

*Primary Examiner*—Rita J Desai
*Assistant Examiner*—David K O'Dell
(74) *Attorney, Agent, or Firm*—Heslin Rothenberg Farley & Mesiti P.C.

(57) ABSTRACT

Processes are disclosed for preparing piperidine derivative compounds of the formulae I, II or III:

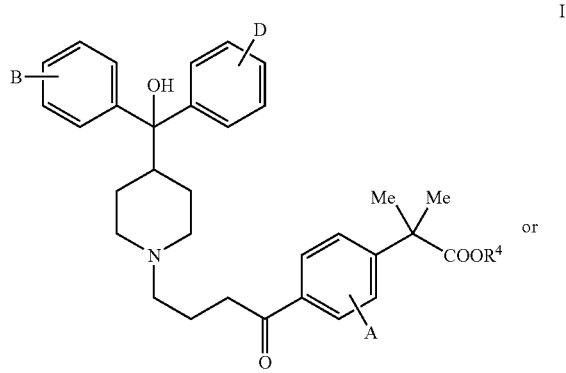

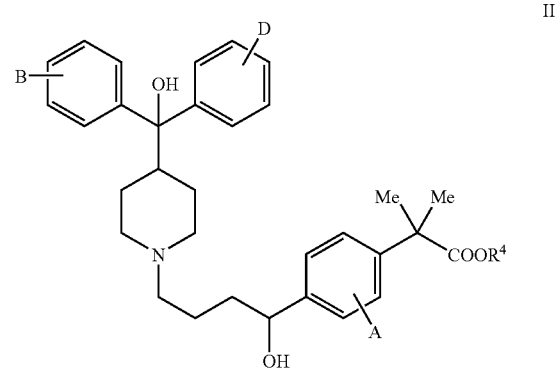

-continued
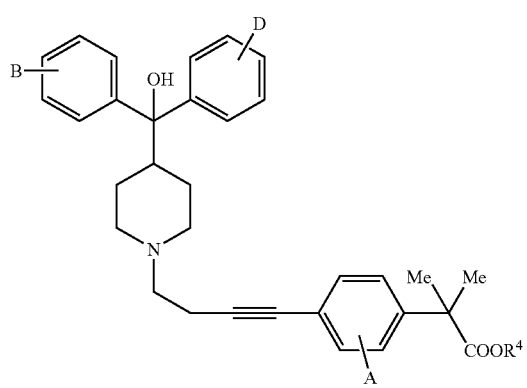
III
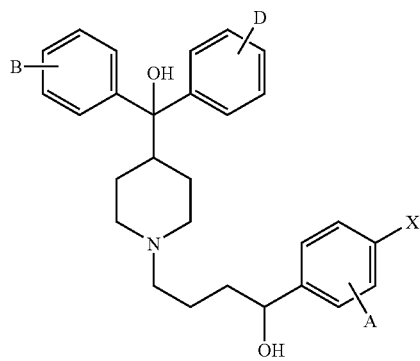
IIa
The processes involve reacting a compound of formula Ia, IIa or IIIa
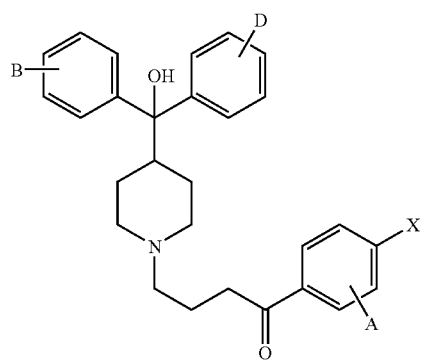
Ia
or
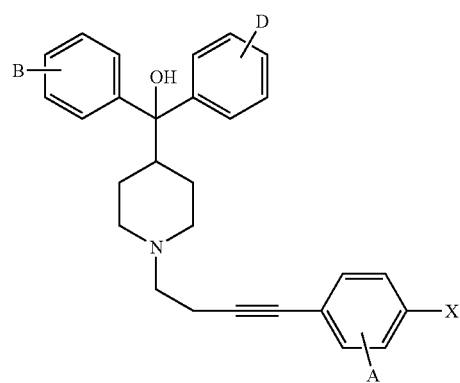
IIIa
with isobutyrate or an isobutyrate equivalent.
14 Claims, No Drawings

PROCESS FOR PRODUCTION OF PIPERIDINE DERIVATIVES

FIELD OF THE INVENTION

The present invention relates to processes for the production of piperidine derivatives.

BACKGROUND OF THE INVENTION

Fexofenadine, 4-[4-[4-(hydroxydiphenylmethyl)-1-piperidinyl]-1-hydroxybutyl]-α-α-dimethylphenylacetic acid, formerly known as terfenadine carboxylic acid metabolite, is a potent non-sedating antihistamine sold by Aventis in the United States under the tradename ALLEGRA® and elsewhere in the world under the tradename TELFAST®.

The importance of commercially viable syntheses of fexofenadine is attested to by the scores of patents to fexofenadine processes. Piperidine derivatives related to fexofenadine are disclosed in the following U.S. Pat. Nos. 4,254,129; 4,254,130; 4,285,957; and 4,285,958. In these patents, 4-[4-[4-(hydroxydiphenylmethyl)-1-piperidinyl]-1-hydroxybutyl]-α,α-dimethylbenzeneacetic acid and related compounds are prepared by alkylation of a substituted piperidine derivative of the formula:

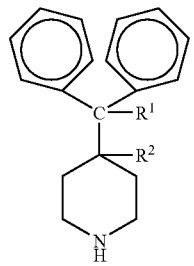

with an ω-haloalkyl substituted phenyl ketone of the formula:

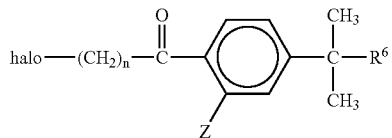

wherein the substituents halo, $R^1$, $R^2$, n, Z, and $R^6$ are described in column 6 of U.S. Pat. No. 4,254,130.

U.S. Pat. No. 4,254,130 indicates that ω-haloalkyl substituted phenyl ketones, wherein Z is hydrogen, are prepared by reacting an appropriate straight or branched lower alkyl $C_{1-6}$ ester of α-α-dimethylphenylacetic acid with a compound of the following formula:

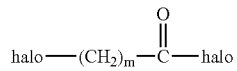

under the general conditions of a Friedel-Crafts acylation, wherein halo and m are described in column 11 of U.S. Pat. No. 4,254,129. The reaction is carried out in carbon disulfide as the preferred solvent.

A more recent approach via Friedel-Crafts acylation with succinic anhydride, condensation with the piperidine and reduction of the ketone and amide carbonyls has issued as U.S. Pat. No. 6,743,941.

It has been found that the Friedel-Crafts methods have two significant shortcomings: (1) only acyl halides or anhydrides can be used; (2) in the particular case of the fexofenadine intermediate phenyl ketones, a higher regioselectivity of the Friedel-Crafts acylation would be desirable.

In another approach, which is the subject of a series of patents to D'Ambra and others (U.S. Pat. Nos. 5,589,487; 6,153,754 and 6,201,124), fexofenadine is synthesized by a regioselective method employing non-Friedel-Crafts acylation. The processes of the D'Ambra patents involve acylation of an aromatic ring at a position already para-substituted with a reactive species. Acylation can be carried out by a variety of techniques, including a butyl derivative acylating agent, a 4-(α,α-disubstituted)-toluic acid derivative acylating agent, or an organometallic coupling reaction. Since such procedures do not involve replacement of hydrogen on an aromatic ring, they are distinguished from electrophilic aromatic substitutions like the Friedel-Crafts acylation reaction.

Other procedures for producing fexofenadine are disclosed in PCT Application Nos. WO95/00482, WO94/03170, and WO95/00480. A more recent approach is outlined in US published application 2003/0166682, in which an intermediate nitrile is hydrolyzed to fexofenadine.

The present invention is directed toward an improved process for preparation of fexofenadine.

SUMMARY OF THE INVENTION

The present invention relates to processes for preparing piperidine derivative compounds of the formulae I, II or III:

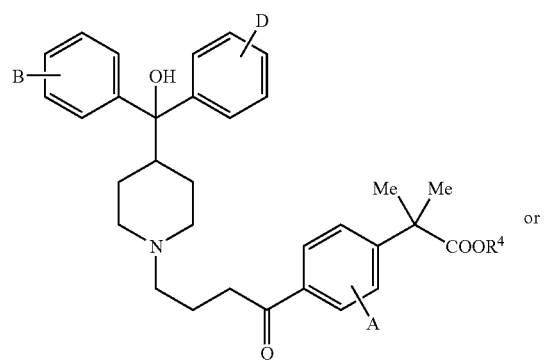

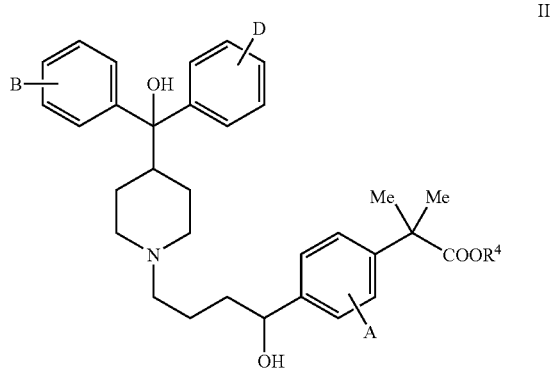

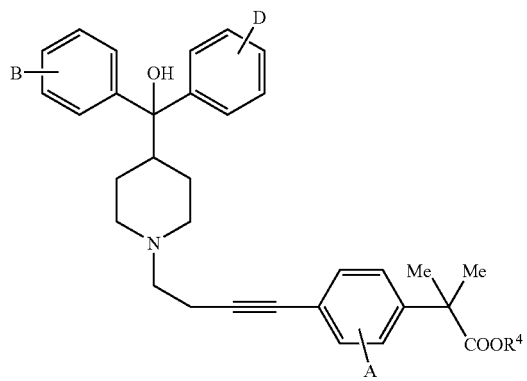

III

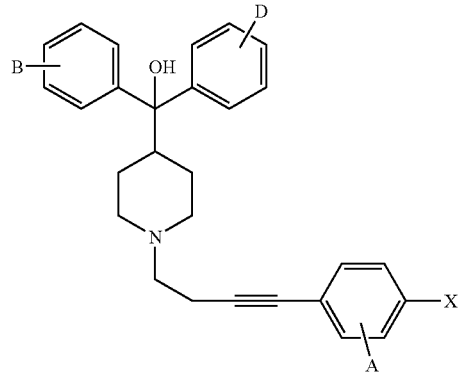

IIIa wherein

R⁴ is H, alkyl or aryl;

A, B, and D are the substituents of their rings, each of which may be different or the same, and are selected from the group consisting of hydrogen, fluorine, chlorine, alkyl, aryl, hydroxyl, alkoxy, and aryloxy. The process comprises providing a compound of formula Ia, IIa or IIIa wherein X is any group displaceable via an oxidative metallic addition, and converting the compound of formula Ia, IIa or IIIa to I, II or III respectively by reacting with isobutyrate or an isobutyrate equivalent.

In another aspect the invention relates to a process for preparing an α,α-dimethyl-4-acylphenylacetate of the formula V, VI or VII:

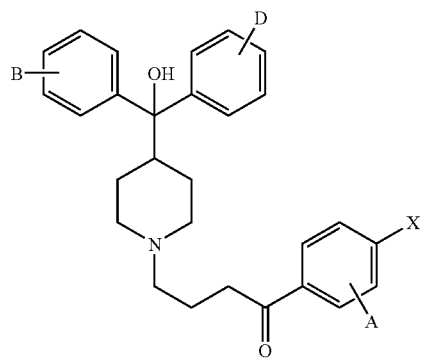

Ia

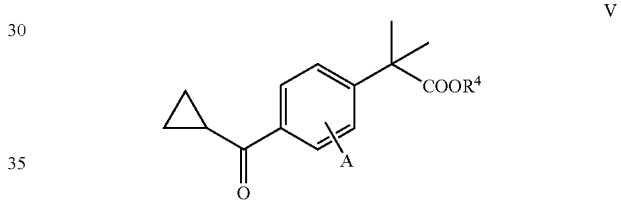

V

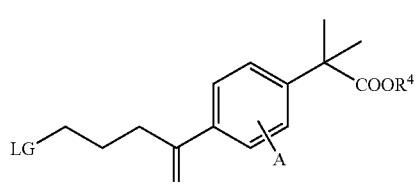

VI

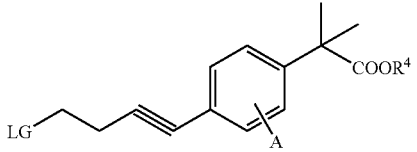

VII

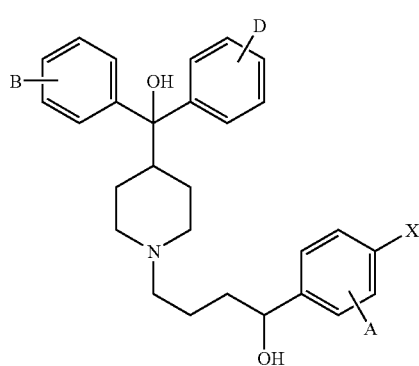

IIa wherein LG is a leaving group displaceable by a secondary amine. The process comprises providing a compound of formula Va, VIa or VIIa:

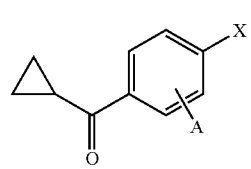

Va

-continued

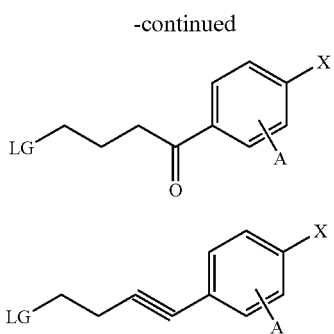

and converting the compound of formula Va, VIa or VIIa to V, VI or VII respectively by reacting with isobutyrate or an isobutyrate equivalent.

In another aspect the invention relates to compounds of formula

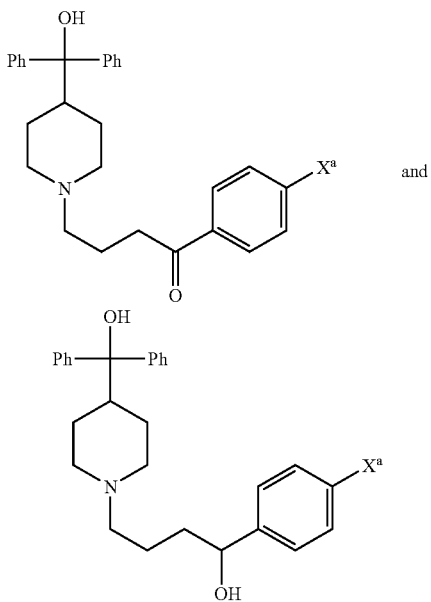

in which $X^a$ is —$OSO_2R^5$, —$N_2^+$, —OH or —$B(OR^6)(OR^7)$, wherein $R^5$ is chosen from fluoro, alkyl, fluoroalkyl, aryl, heteroaryl and substituted aryl; and $R^6$ and $R^7$ are chosen from H and $C_1$-$C_{20}$ hydrocarbon.

DETAILED DESCRIPTION OF THE INVENTION

Throughout this application, various references are referred to. The disclosures of each of these publications in their entireties are hereby incorporated by reference as if written herein.

Definitions

In this specification the terms and substituents are defined when introduced and retain their definitions throughout.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s-and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ Hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, etc. refer to alkyl, aryl or cycloalkyl, wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group that is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry [See e.g. *Protective Groups in Organic Synthesis* by T. W. Greene and P. G. M. Wuts, 2nd Edition; John Wiley & Sons, New York (1991)].

The abbreviations Me, Et, Ph, Tf, Ts and Ms represent methyl, ethyl, phenyl, trifluoromethanesulfonyl, toluensulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The present invention relates to processes for preparing piperidine derivative compounds of the formulae I, II or III. In these compounds, A, B, and D may be different or the same, and are selected from the group consisting of hydrogen, fluorine, chlorine, alkyl, aryl, hydroxyl, alkoxy, and aryloxy. Examples of compounds of formula I, II and III are those in which all of A, B and D are hydrogen and those in which A is hydrogen and B and D are halogens, e.g. fluorine, at the para positions.

The compounds of formula I may be reduced with hydrides, boranes or other reducing agents, as well known in the art, [see e.g. U.S. Pat. Nos. 5,589,487 and 6,743,941] to produce fexofenadine. The compounds of formula II in which $R^4$ is alkyl or aryl may be hydrolyzed to produce fexofenadine. When $R^4$, A, B, and D are all hydrogen, the compounds of formula II are fexofenadine and are produced by a direct single-step reaction. The compounds of formula III may be converted to compounds of formula I by the procedure described by Kawai et al. *J. Org. Chem.* 59, 2620-2622 (1994).

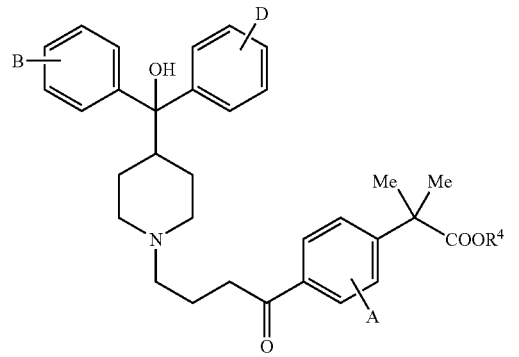

I

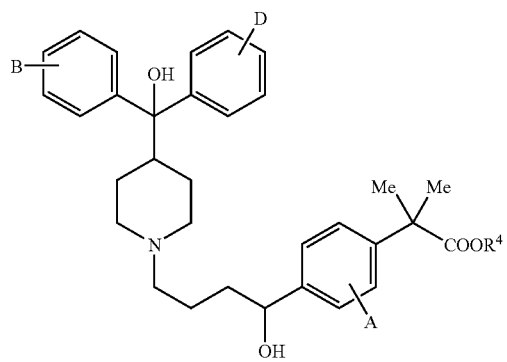

II

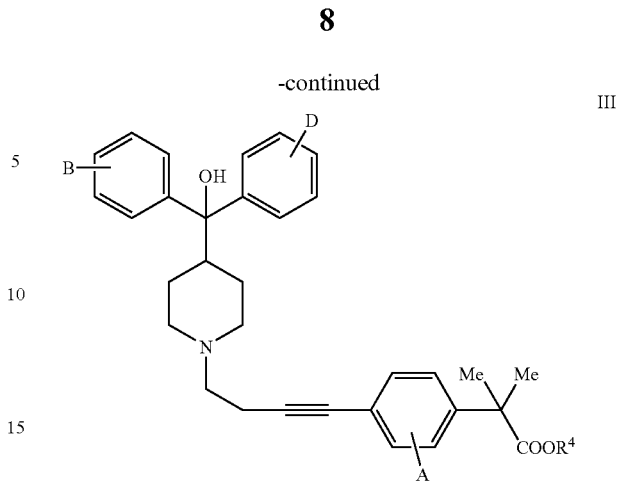

III

The compounds of formulae I, II and III are prepared by a process in which a compound of formula Ia, Ia or IIIa

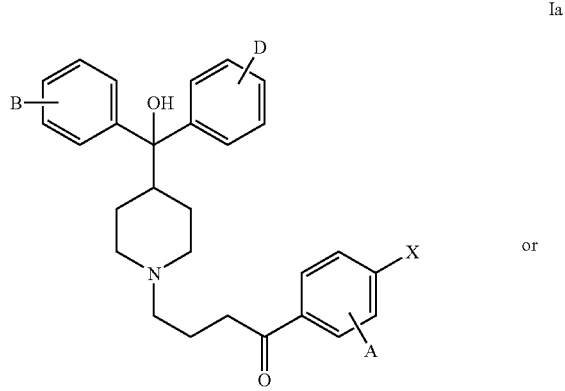

Ia or

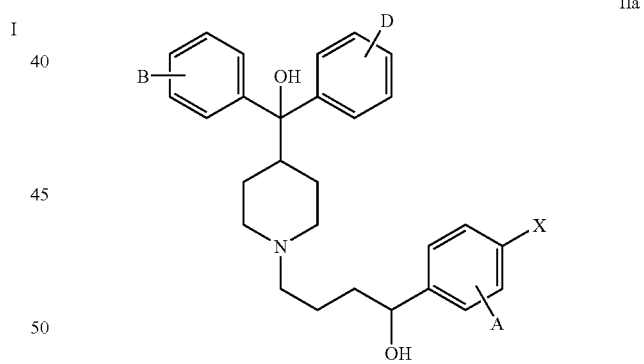

IIa

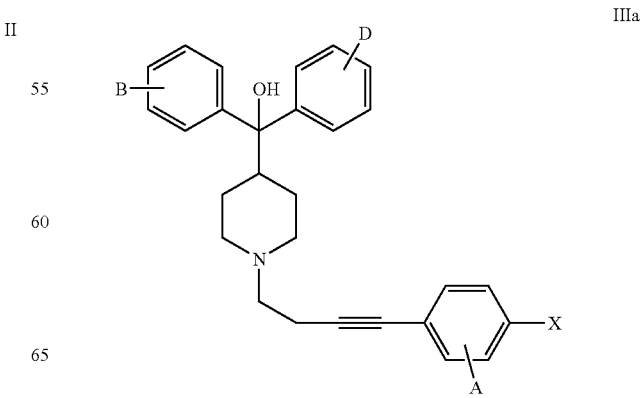

IIIa is reacted with isobutyrate or an isobutyrate equivalent. The substituent X may be chlorine, bromine, iodine, —OSO$_2$R$^5$, —N$_2^+$, —OH or —B(OR$^6$)(OR$^7$), wherein R$^5$ is chosen from fluoro, alkyl, fluoroalkyl, aryl, heteroaryl and substituted aryl; R$^6$ and R$^7$ are chosen from H and C$_1$-C$_{20}$ hydrocarbon, including cyclic structures, e.g. dioxaboroles. Compounds in which X is —OSO$_2$R$^5$, may be prepared from compounds in which X is —OH by sulfonation with the appropriate sulfonyl halide or anhydride in the presence of a base, as well known in the art. Compounds in which X is —N$_2^+$ may be prepared from the corresponding aniline or nitrobenzene by processes well known in the art. [See e.g. Herr et al. *Org. Proc. Res. Dev.* 6, 677-681 (2002) and Siegrist et al. *Org. Proc. Res. Dev.* 7, 429-431 (2003).] Compounds in which X is —B(OR$^6$)(OR$^7$) may be prepared from the corresponding halides by the method of Ishiyama et al. [*J. Org. Chem.* 60, 7508-7510 (1995)].

The isobutyrate or an isobutyrate equivalent may be of the formula VIII or IV:

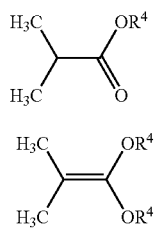

wherein R$^8$ is a protecting group for a ketene acetal, [See *Protective Groups in Organic Synthesis* by T. W. Greene, op. cit.] The protecting group for a ketene acetal may be a simple alkyl, such as methyl or ethyl, a dialkylphosphoryl or, preferably, a trialkylsilyl group, such as trimethylsilyl or t-butyldimethylsilyl. The compounds of formula VIII are commercially available or are synthesized by procedures well-known in the art.

The compounds of formula IV are also known in the art and may be synthesized as described by Liu and Hartwig [*J. Am. Chem. Soc.* 126, 5182-5191 (2004)]. The isobutyrate or isobutyrate equivalent may also be of the formulae IX-XII:

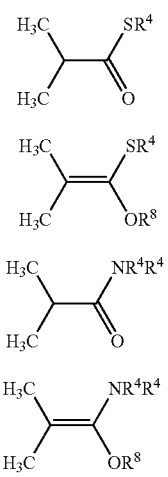

although these equivalents are less preferred. As will be evident to the artisan, the conditions for the final hydrolysis of ester to carboxylate to prepare fexofenadine will be modified to accommodate the thioester or amide.

The coupling reactions are carried out in a suitable solvent in the presence of an appropriate catalyst for about 1 to 120 hours and at temperatures of about −78° C. to the reflux temperature of the solvent. Suitable solvents for coupling include: hydrocarbon solvents, such as benzene, toluene, xylene, or cyclohexane; halogenated hydrocarbons, such as chlorobenzene, dichloroethane, methylene chloride, chloroform, or carbon tetrachloride; carbon disulfide; dimethylformamide; ethereal solvents, like tetrahydrofuran and diethylether; or dioxane.

The reaction between the compounds of formulae I-III and IV or VIII is catalyzed by a transition metal. The transition metal catalyst is a Group 8B transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal. The preferred catalysts for condensations are palladium acetate, palladium chloride, palladium bromide, palladium acetylacetonate, bis(tri-o-tolyl)phosphine palladium dichloride, tetrakis(triphenylphosphine)palladium [(Ph$_3$P)$_4$Pd] and bis(dibenzylideneacetone) palladium [(dba)$_2$Pd].

The chelating ligand my be a neutral molecule or charged ion. The chelating ligand is also required to contain at least one element from Group 5B of the Periodic Table, preferably, at least one element of nitrogen, phosphorus, or arsenic, and more preferably nitrogen or phosphorus. Examples include tri-(o-tolyl)phosphine and triphenylphosphine. Preferred ligands for the coupling with VIII are 1,1'-bis(di-o-tolylphosphino)ferrocene (DTPF); 1,1'-bis(diphenylphosphino)ferrocene (DPPF); 1-di-t-butylphosphino-2-methylaminoethyl ferrocene; [2'-(diphenylphosphino)[1,1'-binaphthalen]-2-yl] diphenylphosphine oxide (BINAP) and 2,2'-bis(di-p-tolylphosphino)-1,1'-binaphthyl (tol-BINAP). Preferred ligands for the coupling with IV are trialkyl or triarylphosphines, such as tri-t-butylphosphine.

Conditions for metal catalyzed couplings are described with references in Diederich and Stang, *Metal-Catalyzed Cross-Coupling Reactions*; Wiley-VCH (1998) and in particular detail in U.S. Pat. No. 6,057,456. In addition to palladium catalysts, as described below, one may employ other transition metals.

In formula Ia-IIIa, as well as in Va and VIa below, X is preferably bromide or triflate, as shown in the examples below, but other substituents suitable for metal catalyzed coupling reactions may be used in their place. For example, diazonium salts may be used as described in Sakakura et al *JCSP*1 1994, 283-288. It will be apparent to the person of skill that, when A is chlorine, in order to have reasonable yields of single positional isomers, X should be other than chlorine.

When the starting material is of the formula VIII, a base must be used. Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; alkali metal aryl oxides, such as potassium phenoxide; alkali metal amides, such as lithium amide; tertiary amines, such as triethylamine and tributylamine; (hydrocarbyl)ammonium hydroxides, such as benzyltrimethylammonium hydroxide and tetraethylammonium hydroxide; diaza organic bases, such as 1,8-diazabicyclo[5.4.0]-undec-7-ene and 1,8-diazabicyclo-[2.2.2.]-octane, and silyl compounds such as potassium hexamethyldisilazide (KN(Si(CH$_3$)$_3$)$_2$). Preferably, the base is an alkali alkoxide or a silyl-containing compound. The molar ratio of base to Ia, IIa or IIIa ranges from about 1:1 to about 3:1, and is usually between about 1:1 and 2:1.

When the starting material is of the formula IV, a metal salt is used instead of a base. Exemplary salts include ZnF$_2$ and Zn(OtBu)$_2$.

In another aspect the invention relates to a process for preparing an α,α-dimethyl-4-acylphenylacetate of the formula V, VI or VII:

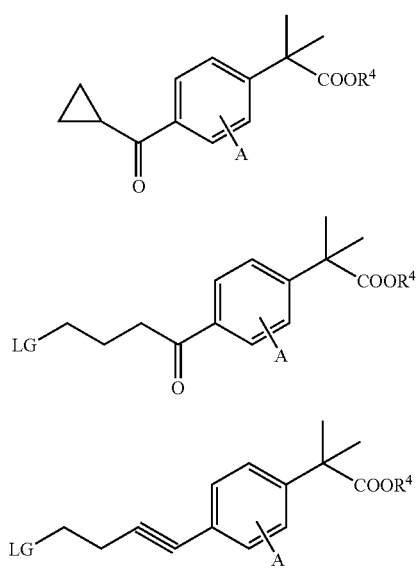

V

VI

VII wherein LG is a leaving group displaceable by a secondary amine, particularly a group displaceable by a piperidine, for example a halogen or a sulfonate. LG is preferably bromine, chlorine, methansulfonate, toluenesulfonate or triflate. The process comprises providing a compound of formula Va, VIa or VIIa:

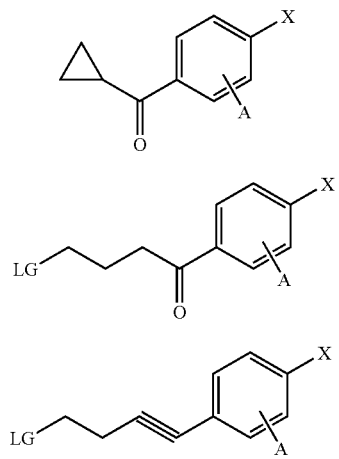

Va

VIa

VIIa and converting the compound of formula Va, VIa or VIIa to V, VI or VII respectively by reacting with isobutyrate or an isobutyrate equivalent. The process parallels the process shown above for I, II and III from Ia, IIa and IIIa in that the reaction conditions and reagents are substantially the same. Compounds of formula Va and VIa, in which A is hydrogen are commercially available from Acros Organics, Geel, Belgium.

The compounds of formula VIIa may be prepared according to the method of Godt [*J. Org. Chem.* 62, 7471(1997)]:

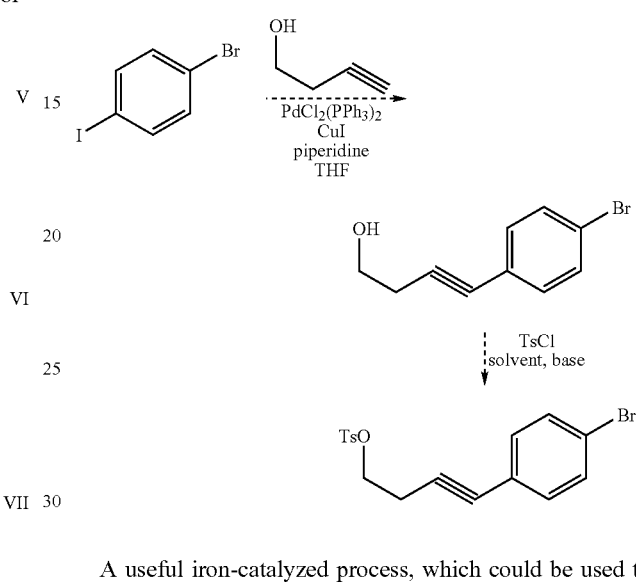

A useful iron-catalyzed process, which could be used to synthesize any of I-VII, is described by Fürstner et al *J. Am. Chem. Soc.* 124, 13856-13863 (2002):

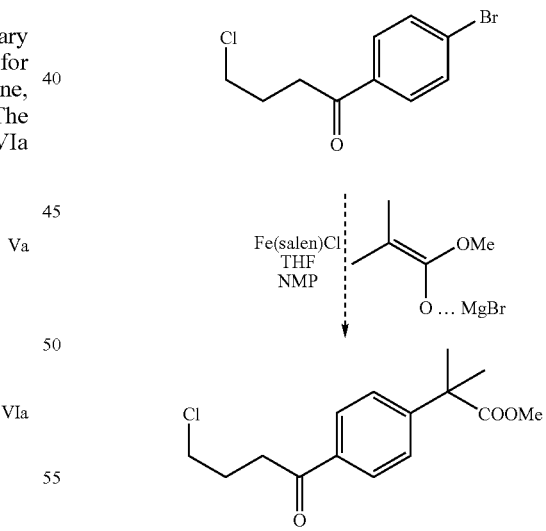

The α,α-dimethyl-4-acylphenylacetates of the formulae V, VI and VII may be further reacted with a piperidine derivative as described in U.S. Pat. Nos. 4,550,116; 5,750,703; 6,153,754; 6,242,606 and others. Exemplary processes that fall within the scope of the invention are illustrated in the schemes below for the synthesis of fexofenadine. These schemes also illustrate the interrelatedness of the processes and intermediates.

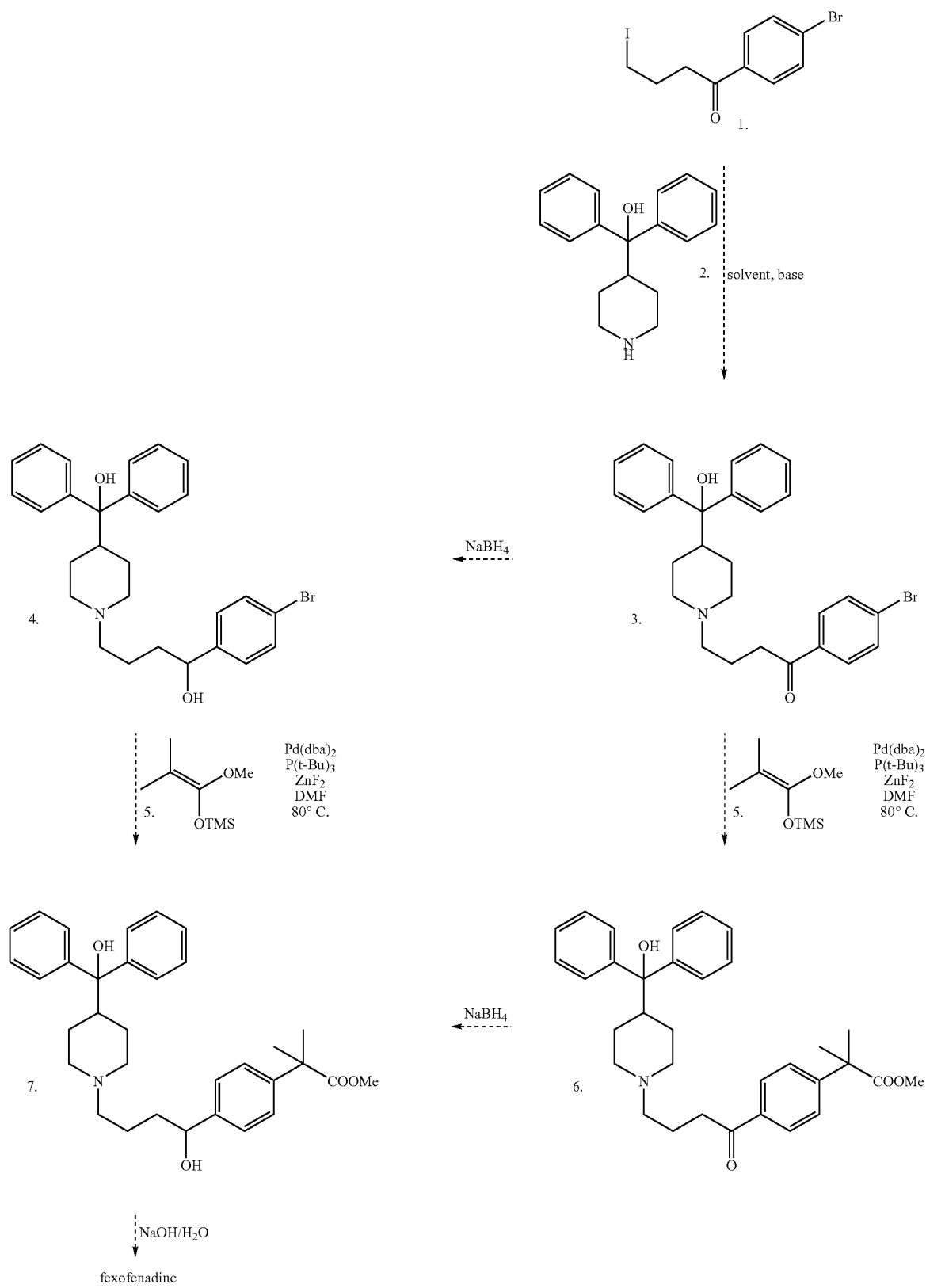

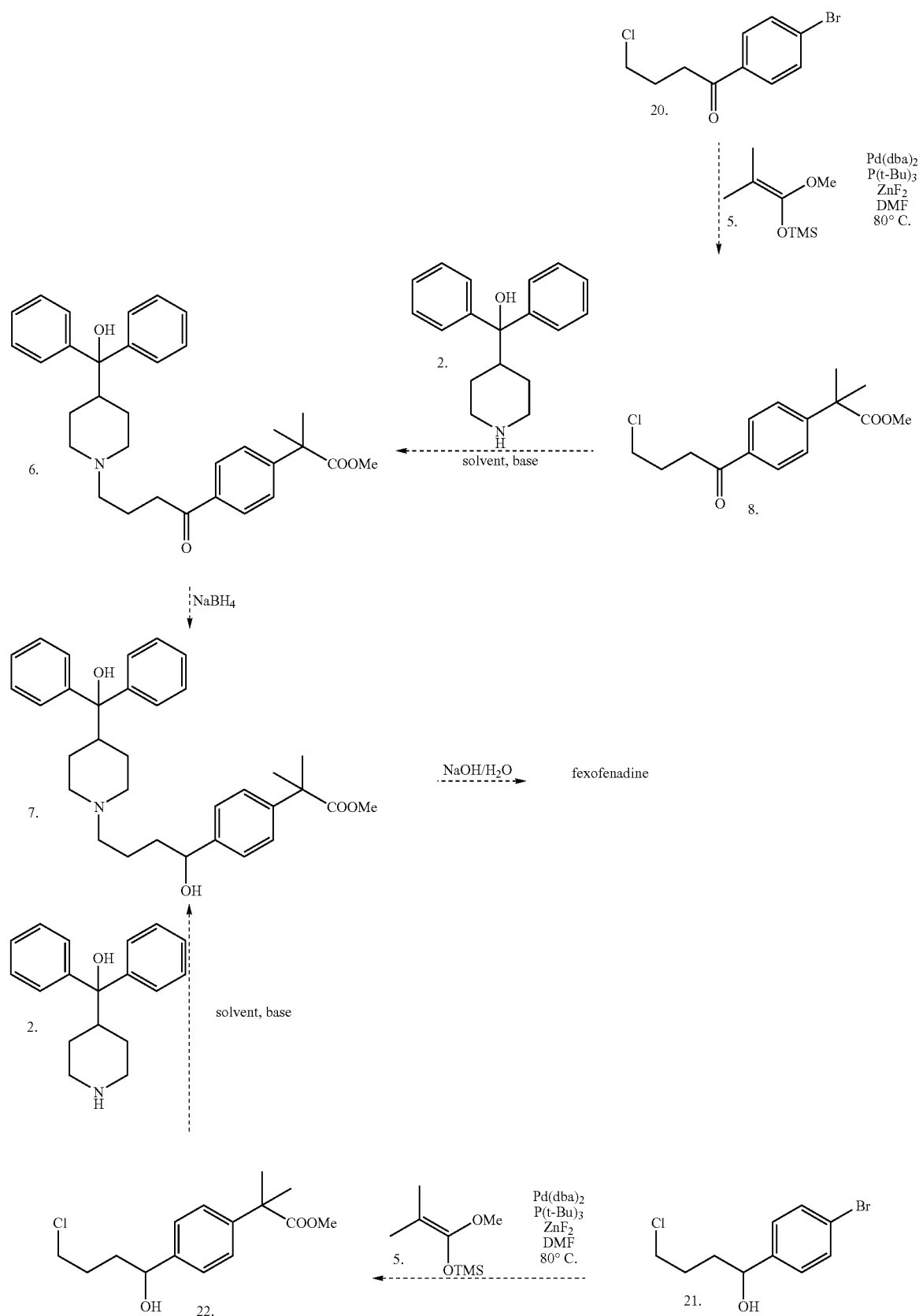
Scheme 2

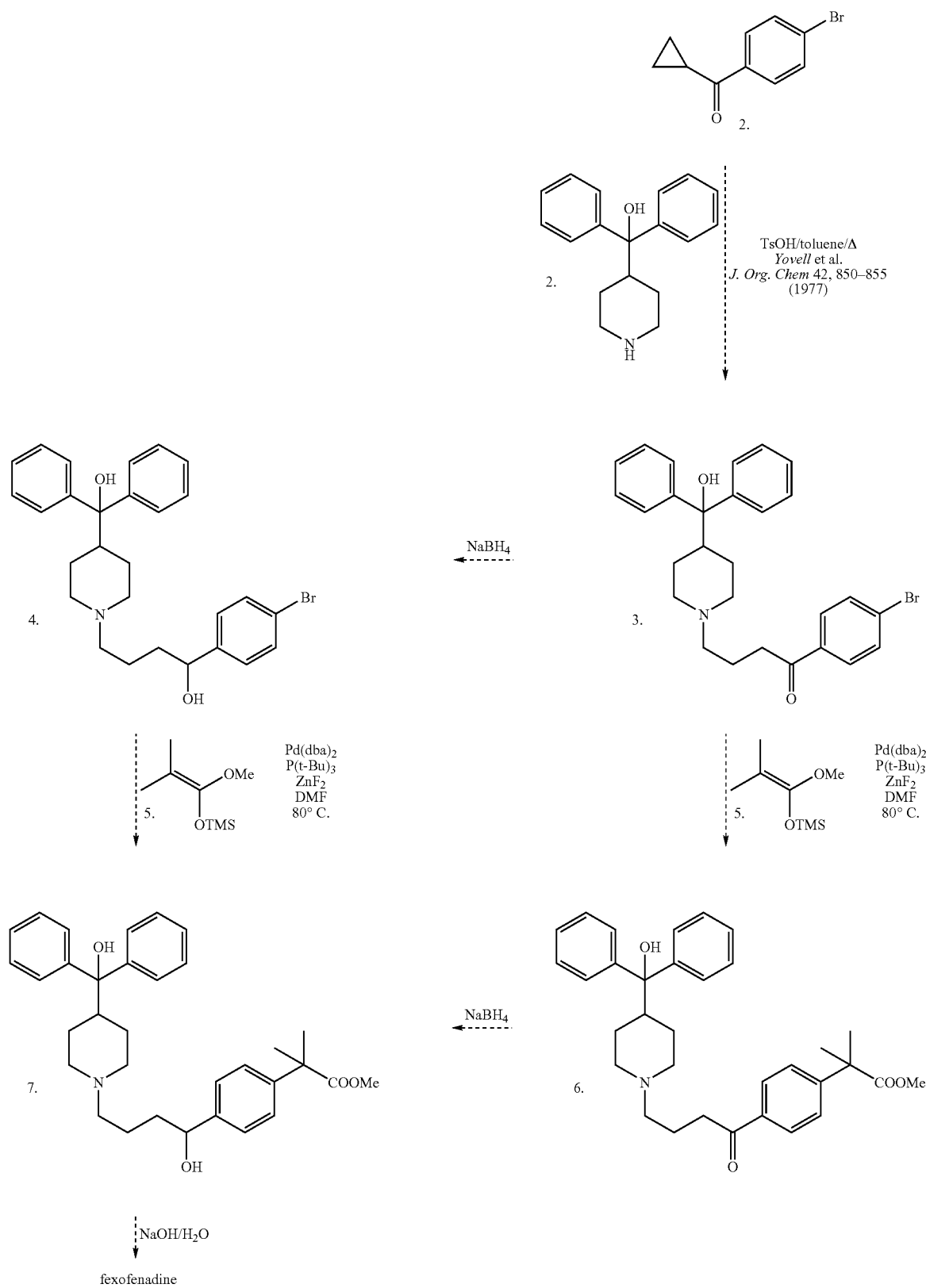

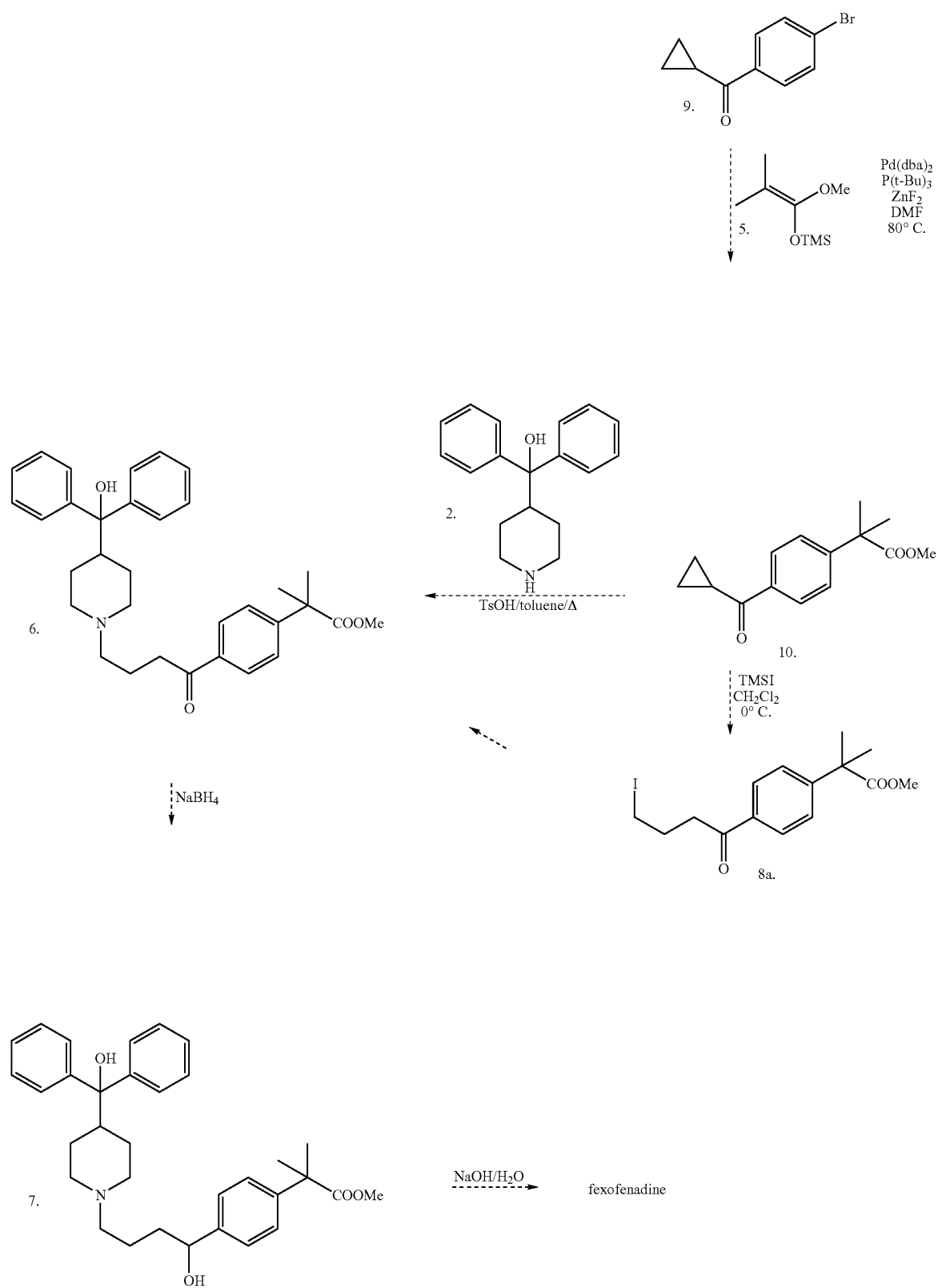
Scheme 4

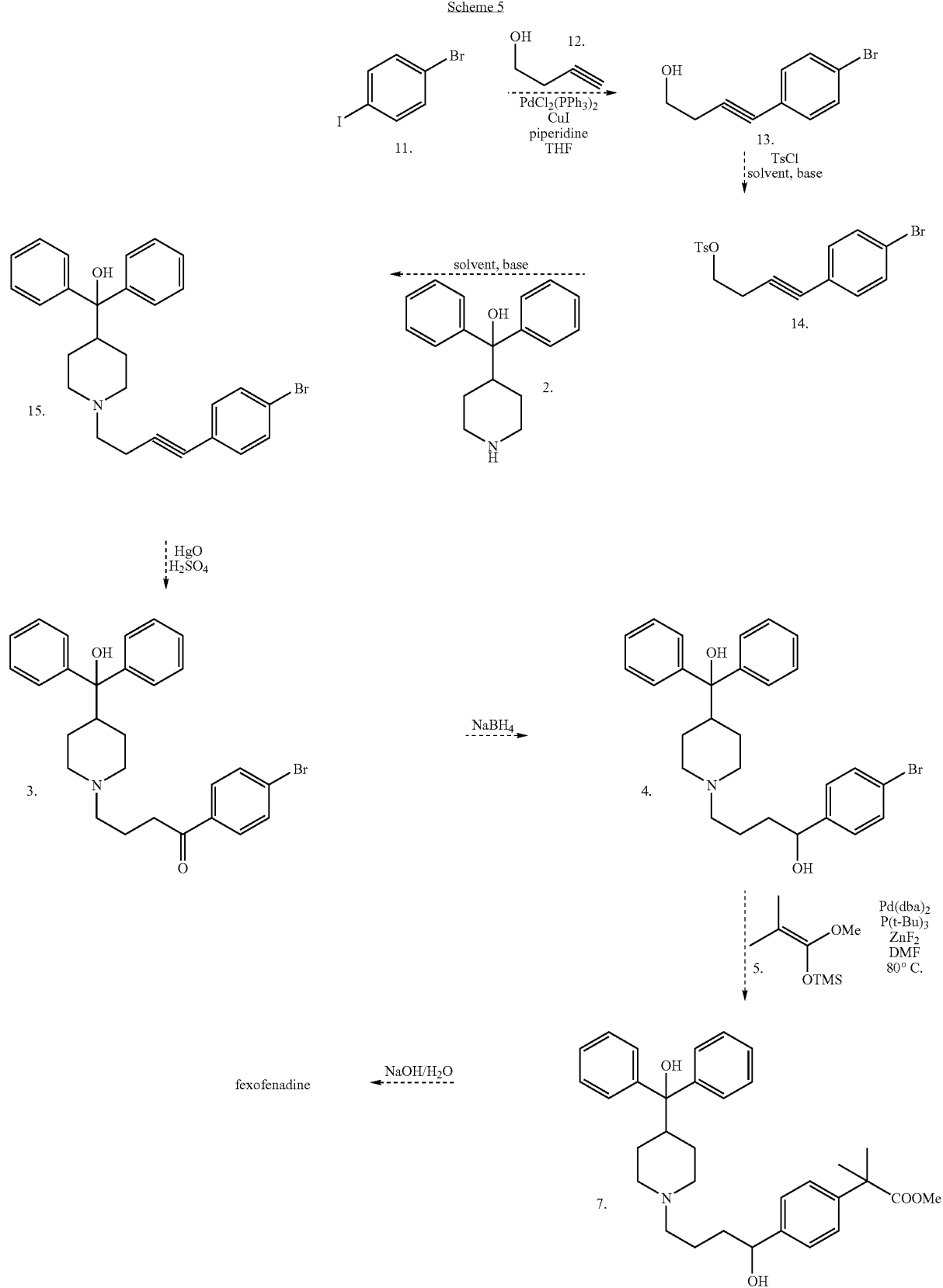

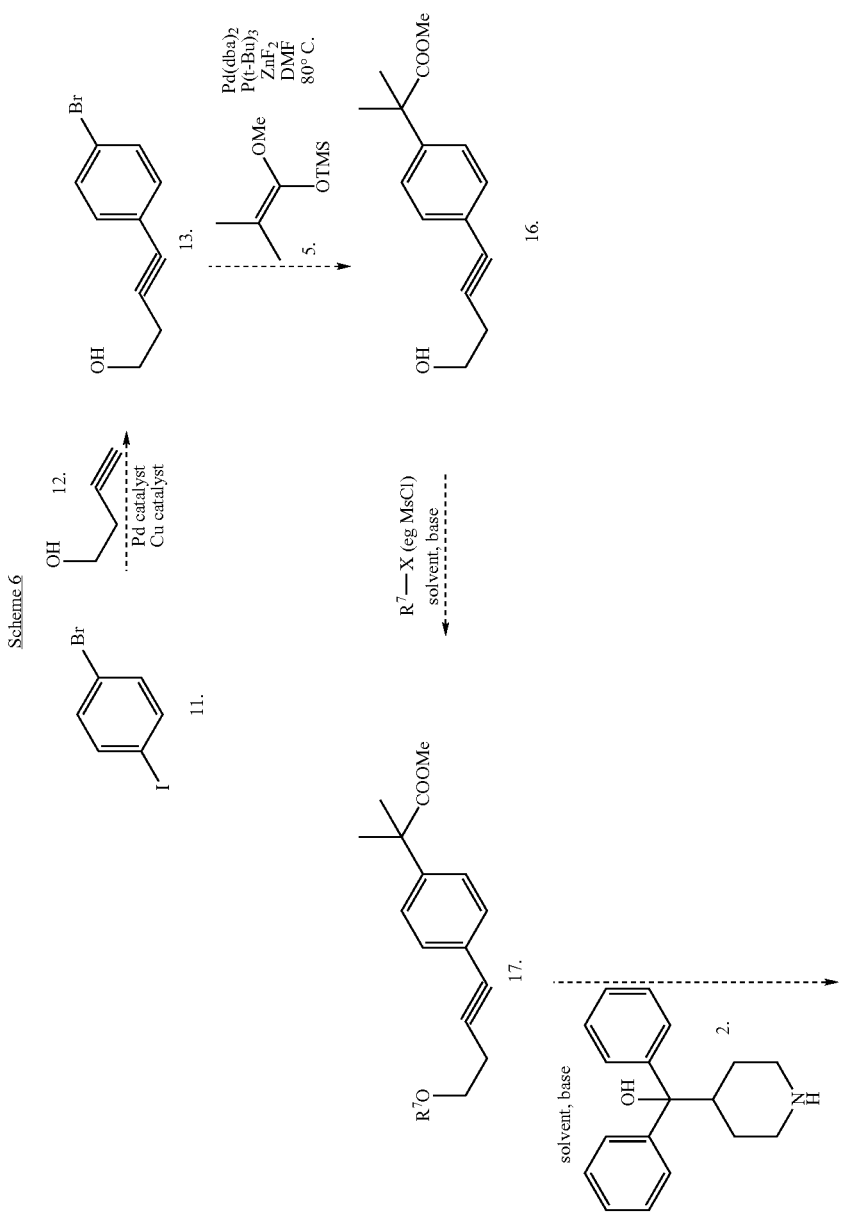

-continued
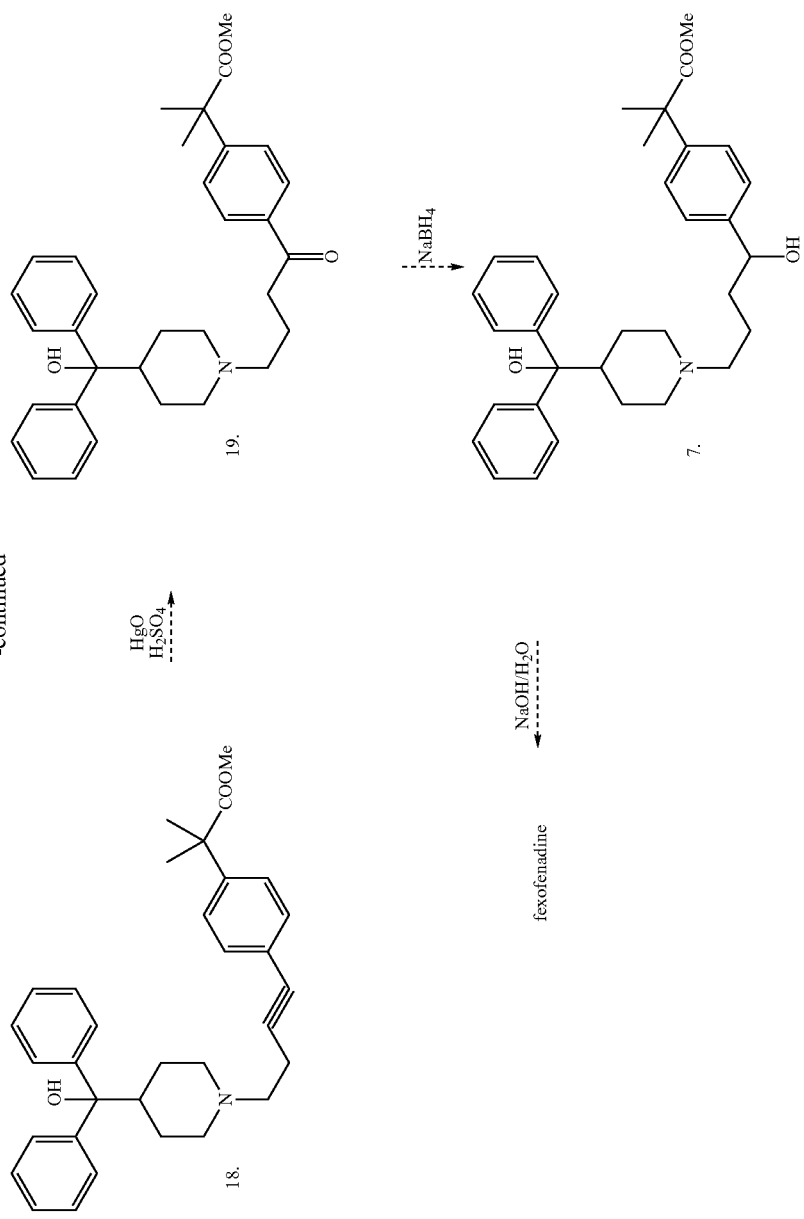

EXAMPLE 1

One gram of 9 was dissolved in 20 mL of DMF and 18 mg of P(tBu)$_3$, 41 mg of Pd(dba)$_2$, 230 mg of ZnF$_2$ and 1.2 g of 5 were added. A mixture was stirred at 80° for 18 hours, cooled to room temperature, diluted with ether and washed with water. The organic layer was dried over sodium sulfate, filtered and stripped in vacuo. The resulting product was flash chromatographed on silica gel using 4:1 hexane ethyl acetate to yield 1.0 g (91%) of 10. A repeat of the reaction on larger scale using 15 g of 9 provided 15.2 g (93%) of 10.

EXAMPLE 2

Five grams of 9 was dissolved in 50 mL of methylene chloride and cooled to 0° C. To the solution was added 5.78 g of trimethylsilyl iodide. The mixture was stirred for 30 minutes and excess sodium bisulfite solution was added with vigorous stirring at room temperature. The layers were separated and the aqueous layer extracted twice with methylene chloride. Combined organic layers were dried, filtered and stripped in vacuo to provide 7.7 g (98%) of 1. The reaction was repeated on a larger scale using 15 g of 9 to produce 22.5 g of 1 (96%) yield.

EXAMPLE 3

Six grams of potassium carbonate, 5.8 g of piperidine 2 and 7.6 g of 1 were combined in 100 mL of DMF. The suspension was stirred at room temperature until TLC in 4:1 hexane-ethyl acetate indicated a complete reaction. The reaction mixture was poured into 400 mL of water and extracted three times with methylene chloride. The combined organic extracts were dried, filtered and reduced in vacuo. The resulting product was flash chromatographed on silica gel using ethyl acetate containing 10% triethylamine to yield 7.0 g (66%) of 3.

EXAMPLE 4

Seven grams of 3 was dissolved in 100 mL of methanol, cooled to 0° C. and 1.1 g of sodium borohydride was added. The mixture was stirred 1 hour, concentrated and partitioned between ethyl acetate and saturated aqueous sodium bicarbonate. The bicarbonate layer was extracted twice with ethyl acetate, the combined organic layers were dried over sodium sulfate and the solution was reduced in vacuo to provide 7.0 g (100%) of 4.

EXAMPLE 5

Two grams of 4 was dissolved in 30 mL of DMF. To this were added 16.2 mg of P(tBu)$_3$, 36.6 mg of Pd(dba)$_2$, 209 mg of ZnF$_2$ and 1.056 g of 5. The mixture was heated at 80° C., cooled, diluted with ether and worked up as in example 1. The resulting product was flash chromatographed on silica gel using 9:1 ethyl acetate-triethylamine to provide 450 mg (21.4%) of 7.

EXAMPLE 6

One hundred fifty milligrams of 7 was slurried in 5 mL of water and 10 mL of methanol. To the slurry was added 175 mg of sodium hydroxide. The slurry was refluxed for one hour, cooled to room temperature and the methanol removed in vacuo. The resulting aqueous solution was distributed between water and chloroform, the chloroform layer was discarded, the aqueous layer was adjusted to pH 2.3 and extracted with chloroform. The organic layer was dried, filtered and reduced in vacuo to provide fexofenadine.

EXAMPLE 7

Five grams of 1 was combined with 3.8 g of 2 and 2.0 g of potassium carbonate and 80 mL of DMF. The mixture was stirred at room temperature for two hours, poured into 400 mL of water and extracted three times into methylene chloride. The combined organic layers were dried, filtered and reduced in vacuo. The resulting product was flash chromatographed on silica gel using 9:1 ethyl acetate-triethylamine to provide 4.2 g (60%) of 3.

EXAMPLE 8

Two grams of 3, 90 mg of P(tBu)$_3$, 300 mg of Pd(dba)$_2$, 250 mg of ZnF$_2$ and 1.1 g of 5 were dissolved in 330 mL of DMF under argon. The mixture was heated to 80° for two hours, cooled to room temperature, diluted with ether and worked up as described in example 1. The resulting product was filtered through silica to provide 1.3 g (62%) of 6.

EXAMPLE 9

Two grams of 20, 170 mg of P(tBu)$_3$, 560 mg of Pd(acac)$_2$, 474 mg of ZnF$_2$ and 2.0 g of 5 were combined in 50 mL of DMF under argon. The mixture was heated to 80° C. and monitored by HPLC. When reaction was complete, the mixture was cooled to room temperature and 250 mL of water was added. The mixture was extracted three times with ether, dried, filtered and reduced in vacuo. The resulting product was flash chromatographed in 4:1 hexane-ethyl acetate to provide 1.89 g (85%) of 8.

EXAMPLE 10

Two grams of the triflate analog of 20 were reacted as in the foregoing example with 134 mg P(tBu)$_3$, 433 mg of Pd (acac)$_2$, 375 mg of ZnF$_2$ and 1.58 g of 5 to provide 1.56 g (90% yield) of 8.

What claimed is:

1. A process for preparing a piperidine derivative compound of formula I:

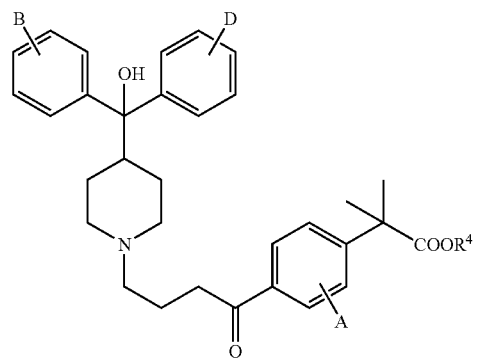

wherein
R$^4$ is selected from the group comprising H, alkyl, and aryl;
A, B, and D are the substituents of their rings, each of which may be different or the same, and are selected from the group consisting of hydrogen, fluorine, chlorine, alkyl, aryl, hydroxyl, alkoxy, and aryloxy;
said process comprising:
(a) reacting a compound of formula VIa

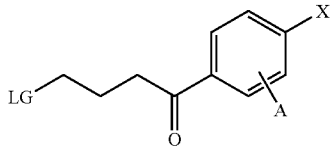
VIa wherein
X is a group chosen from chlorine, bromine, iodine, —OSO$_2$R$^5$, and diazonium salt displaceable via oxidative metallic addition; and
LG is a leaving group displaceable by a secondary amine, said leaving group chosen from chlorine, bromine, iodine, and —OSO$_2$R$^5$, wherein R$^5$ is chosen from alkyl, fluoroalkyl, aryl, and substituted aryl;
with a piperidine compound of formula IX

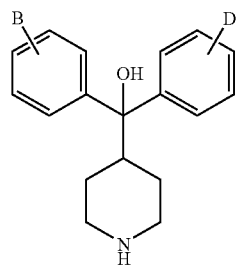
IX in the presence of a base to provide a compound of formula Ia

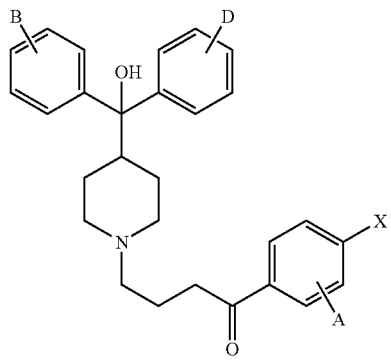
Ia (b) reacting the compound of Ia with an isobutyrate equivalent of formula IV

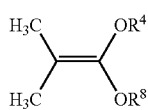
IV wherein R$^8$ is a trialkylsilyl,
in the presence of a transition metal catalyst having a metal selected from the group comprising of Ni and Pd, and ZnF$_2$ to provide the compound of formula I.

2. A process according to claim 1, wherein the compound of formula VIa is prepared by reacting a compound of formula Va

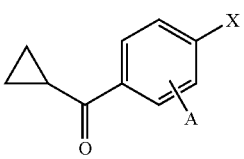
Va with a trialkylsilylhalide.

3. A process according to claim 1 for preparing fexofenadine wherein the compound of formula I is reacted in the presence of a reducing agent, and carrying out further process steps to provide fexofenadine.

4. A process according claim 1 wherein X is displaceable by the isobutyrate equivalent of formula IV by reaction in the presence of a phosphorous compound chosen from trialkyl phosphine, triaryl phosphine, and mixed alky/aryl phosphine, and the transition metal catalyst.

5. A process according to claim 1 wherein R$^8$ is trimethylsilyl.

6. A process according claim 1 for preparing fexofenadine comprising:
(a) reacting a compound of formula VIaa

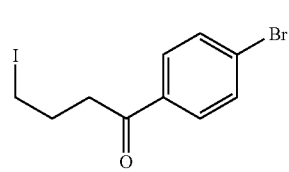
VIaa with a piperidine compound of formula IXaa

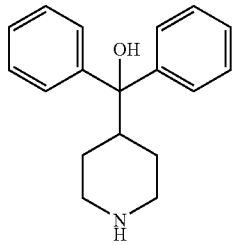
IXaa in the presence of a base to provide a compound of formula Iaa

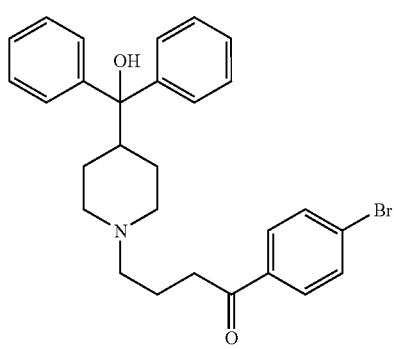
Iaa (b) reacting the compound of formula Iaa wth an isobutyrate equivalent of formula IVa

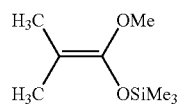  IVa in the presence of Pd(0) catalyst, a trialkyl or triaryl phosphine, and ZnF$_2$ to provide a compound of formula Iaaa

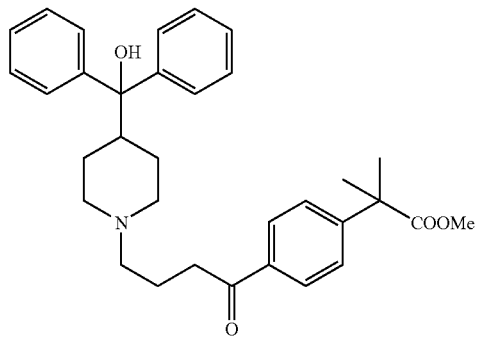  Iaaa (c) and carrying out further processing steps to provide fexofenadine.

7. A process according to claim 6 wherein, the compound of VIaa is prepared by reacting a compound of formula Vaa

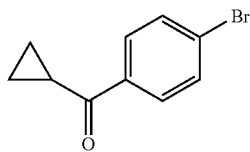  Vaa with a trimethlysilyliodide.

8. A process for preparing a piperidine derivative compound of formula II:

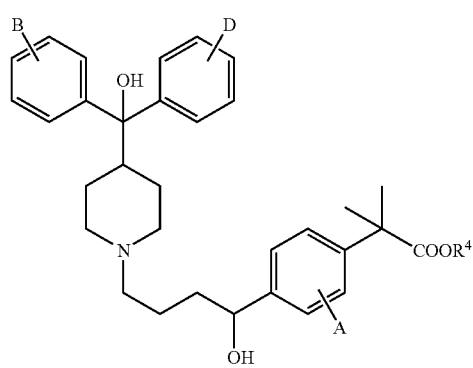  II wherein
R$^4$ is selected from the group comprising H, alkyl, and aryl;
A, B, and D are the substituents of their rings, each of which may be different or the same, and are selected from the group consisting of hydrogen, fluorine, chlorine, alkyl, aryl, hydroxyl, alkoxy, and aryloxy;

said process comprising:

(a) reacting a compound of formula VIa

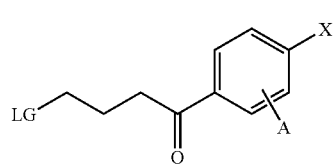  VIa wherein
X is a group chosen from chlorine, bromine, iodine, —OSO$_2$R$^5$, and diazonium salt displaceable via oxidative metallic addition; and
LG is a leaving group displaceable by a secondary amine, said leaving group chosen from chlorine, bromine, iodine, and —OSO$_2$R$^5$, wherein R$^5$ is chosen from alkyl, fluoroalkyl, aryl, and substituted aryl;

with a piperidine compound of formula IX

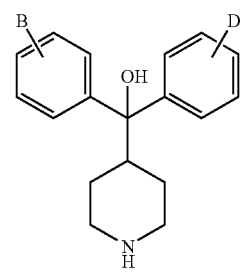  IX in the presence of a base to provide a compound of formula Ia

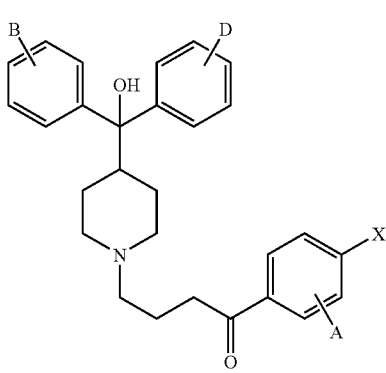  Ia (b) reacting the compound of formula Ia with a reducing agent to provide a compound of formula IIa

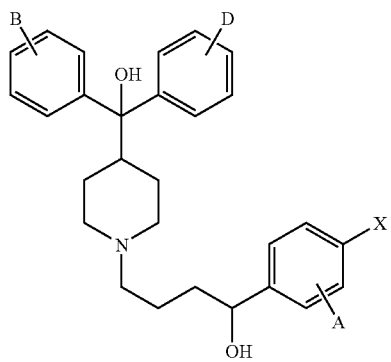

(c) reacting the compound of IIa with an isobutyrate equivalent of formula IV

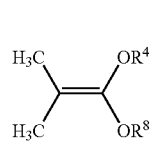

wherein R⁸ is a trialkylsilyl, in the presence of a transition metal catalyst having a metal selected from the group comprising of Ni and Pd, and $ZnF_2$ to provide the compound of formula II.

9. A process according to claim 8, wherein the compound of formula VIa is prepared by reacting a compound of formula Va

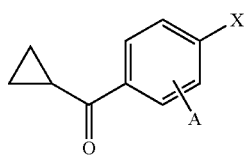

with a trialkylsilylhalide.

10. A process according to claim 8 for preparing fexofenadine wherein the compound of formula II is reacted with a base, and carrying out further process steps to provide fexofenadine.

11. A process according claim 8 wherein X is displaceable by the isobutyrate equivalent of formula IV by reaction in the presence of a phosphorous compound chosen from trialkyl phosphine, triaryl phosphine, and mixed alkyl/aryl phosphine, and the transition metal catalyst.

12. A process according to claim 8 wherein R⁸ is trimethylsilyl.

13. A process according claim 8 for preparing fexofenadine comprising:

(a) reacting a compound of formula VIaa

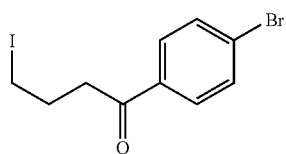

with a piperidine compound of formula IXaa

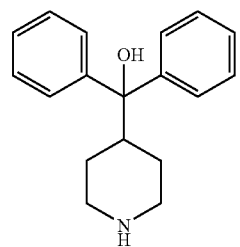

in the presence of a base to provide a compound of formula Iaa

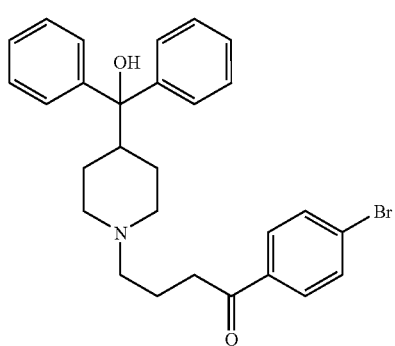

(b) reacting the compound of formula Iaa with a reducing agent to provide a compound of formula IIaa

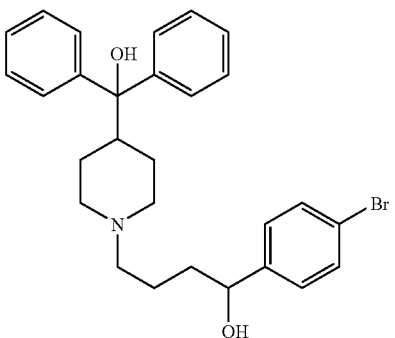

(c) reacting the compound of Iaa wth an isobutyrate equivalent of formula IVa

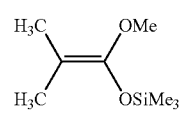

in the presence of Pd(0) catalyst, a trialkyl or triaryl phosphine, and $ZnF_2$ to provide a compound of formula IIaaa IIaaa
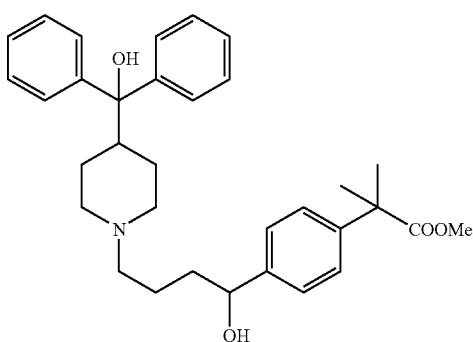
(d) and carrying out further processing steps to provide fexofenadine.
14. A process according to claim 13 wherein, the compound of VIaa is prepared by reacting a compound of formula Vaa
Vaa
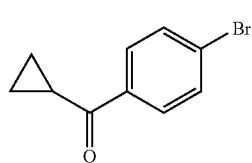
with a trimethlysilyliodide.
* * * * *